US011096871B2

(12) United States Patent
Cao et al.

(10) Patent No.: US 11,096,871 B2
(45) Date of Patent: Aug. 24, 2021

(54) PERSONAL CARE COMPOSITION COMPRISING A COATED POROUS PARTICLE AND DIMETHICONE/VINYLTRIMETHYL-SILOXYSILICATE AND WHITENING AGENT

(71) Applicant: Conopco, Inc., Englewood Cliffs, NJ (US)

(72) Inventors: Xiujuan Cao, Shanghai (CN); Naresh Dhirajlal Ghatlia, Bangalore (IN); Lin Wang, Shanghai (CN); Shuqi Zhu, Shanghai (CN)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 16/647,247

(22) PCT Filed: Aug. 21, 2018

(86) PCT No.: PCT/EP2018/072472
§ 371 (c)(1),
(2) Date: Mar. 13, 2020

(87) PCT Pub. No.: WO2019/052781
PCT Pub. Date: Mar. 21, 2019

(65) Prior Publication Data
US 2020/0253842 A1 Aug. 13, 2020

(30) Foreign Application Priority Data

Sep. 18, 2017 (WO) ................ PCT/CN2017/102040
Oct. 10, 2017 (EP) ..................................... 17195585

(51) Int. Cl.
| | | |
|---|---|---|
| *A61K 8/02* | (2006.01) | |
| *A61K 8/06* | (2006.01) | |
| *A61K 8/25* | (2006.01) | |
| *A61K 8/73* | (2006.01) | |
| *A61K 8/81* | (2006.01) | |
| *A61K 8/87* | (2006.01) | |
| *A61K 8/891* | (2006.01) | |
| *A61K 8/895* | (2006.01) | |
| *A61Q 19/02* | (2006.01) | |
| *A61Q 19/08* | (2006.01) | |

(52) U.S. Cl.
CPC ............ *A61K 8/0279* (2013.01); *A61K 8/062* (2013.01); *A61K 8/25* (2013.01); *A61K 8/731* (2013.01); *A61K 8/8111* (2013.01); *A61K 8/8152* (2013.01); *A61K 8/87* (2013.01); *A61K 8/891* (2013.01); *A61K 8/895* (2013.01); *A61Q 19/02* (2013.01); *A61Q 19/08* (2013.01); *A61K 2800/412* (2013.01); *A61K 2800/43* (2013.01); *A61K 2800/621* (2013.01)

(58) Field of Classification Search
CPC ........ A61K 8/0279; A61K 8/062; A61K 8/25; A61K 8/731; A61K 8/8111; A61K 8/8152; A61K 8/87; A61K 8/891; A61K 8/895; A61K 8/73; A61K 8/81; A61K 8/02; A61K 8/04; A61K 2800/412; A61K 2800/43; A61K 2800/621; A61Q 19/02; A61Q 19/08
See application file for complete search history.

(56) References Cited

U.S. PATENT DOCUMENTS

| | | |
|---|---|---|
| 2004/0005340 A1 | 1/2004 | Patel et al. |
| 2004/0086473 A1* | 5/2004 | Rabe ........................ A61K 8/25 424/63 |
| 2005/0220728 A1 | 10/2005 | Kanji et al. |
| 2005/0244351 A1 | 11/2005 | Reinhart et al. |
| 2007/0258922 A1 | 11/2007 | Wozniak et al. |

FOREIGN PATENT DOCUMENTS

| | | |
|---|---|---|
| EP | 0502769 | 9/1992 |
| JP | 2013103885 | 5/2013 |
| WO | WO0215875 | 2/2002 |
| WO | WO2005060922 | 7/2005 |
| WO | WO2013169506 | 11/2013 |
| WO | WO2014126728 | 8/2014 |

OTHER PUBLICATIONS

Kobo Products tradepaper, MSS-500/3H (Year: 2021).*
Partial Search Report and Written Opinion in EP17195585; dated Apr. 20, 2018.
GNPD Mintel; Silk Base SPF 26 PA++; Amorepacific; Jul. 2017; pp. 1-4; Database accession No. 4946315; XP002779808.
GNPD Mintel; Control Shine and Prime Oil-free Mattifying Primer; Sleek Cosmetics; Aug. 2017; pp. 1-4, Database accession No. 4988275, XP002779807.
Search Report and Written Opinion in EP17195585; dated Sep. 4, 2018.
GNPD Mintel; CC Moisture Base SPF 27 PA++; FamilyMart; Jan. 2015; pp. 1-4, Database accession No. 2892569, XP055517215.
GNPD Mintel; The Bright Up Day Serum; Pola; May 2013; pp. 1-6, Database accession No. 2054806, XP055517245.
GNPD Mintel; Designing Pre Make SPF 25/PA+++; Avon; Nov. 2013; pp. 1-4, Database accession No. 2333812, XP055517238.
Partial Search Report and Written Opinion in PCTEP2018072472; dated Oct. 31, 2018.
Search Report and Written Opinion in PCTEP2018072472; dated Jan. 4, 2019.

(Continued)

*Primary Examiner* — Carlos A Azpuru
(74) *Attorney, Agent, or Firm* — Stephanie Huang

(57) ABSTRACT

Disclosed is a personal care composition comprising: a) a porous particle; b) a film forming polymer; and c) a cosmetically acceptable carrier which is a water and oil emulsion; wherein the porous particle has oil absorption value in the range of 50 g/100 g to 1500 g/100 g; wherein the porous particle is selected from porous silica, cellulose, acrylic polymer, nylon and ethylene/methacylate copolymer hollow sphere coated with porous silica; wherein the film forming polymer is selected from an acrylate polymer, a methacrylate polymer, a urethane polymer or co-polymers thereof; and wherein the composition comprises whitening pigment in an amount of from 0.001 to 2 wt %.

17 Claims, No Drawings

(56) References Cited

OTHER PUBLICATIONS

Written Opinion 3 in PCTEP2018072472; dated Aug. 2, 2019.
IPRP2 in PCTEP2018072472; Dec. 13, 2019.
BISHOP; Sensorial Synergies in Silicone; Shin-Etsu; Jun. 2013; pp. 1-4; Shin-Etsu Silicones of America, Inc.
GNPD Mintel; Blur Me Instant Perfecting Blur; Cosmeticos Natura; Apr. 2016; pp. 1-4; Database accession No. 3921847.
GNPD Mintel; Lasting Mineral BB Cream; Tianjin Yishiban Cosmetic Products; Mar. 2016; pp. 1-3, Database accession No. 3898603.
GNPD Mintel; Instant Skin Smoother Finishing Cream SPF 30; L'Oreal; Jan. 2014; pp. 1-3, Database accession No. 2304058.
GNPD Mintel; Instant Skin Smoother; L'Oreal; Mar. 2013; pp. 1-3, Database accession No. 2020881.
GNPD Mintel; Instant Skin Smoother SPF 30; L'Oreal; Feb. 2013; pp. 1-3, Database accession No. 1993736.
KOBO; Microspheres Spec Sheet; Technical Literature ref MSp-001; Jan. 29, 2015; pp. 1-2.

\* cited by examiner

PERSONAL CARE COMPOSITION COMPRISING A COATED POROUS PARTICLE AND DIMETHICONE/VINYLTRIMETHYL-SILOXYSILICATE AND WHITENING AGENT

CROSS REFERENCE TO RELATED APPLICATIONS

The present application is a U.S. National Phase Application under 35 U.S.C. § 371 of International Application No. PCT/EP2018/072472, filed on Aug. 21, 2018, which claims priority to International Application No. PCT/CN2017/102040, filed Sep. 18, 2017 and European Patent Application No. 17195585.9, filed on Oct. 10, 2017, the contents of which are incorporated herein in their entireties.

FIELD OF THE INVENTION

The present invention relates to a personal care composition. In particular, the personal care composition is directed to providing enhanced skin appearance like improved blurring. This is achieved by including specific porous particles in combination with specific film forming polymers in a personal care composition.

BACKGROUND OF THE INVENTION

Ageing brings with it many changes to the appearance of skin. Of particular concern to individuals wishing to maintain a youthful appearance, is the reduction or elimination of skin imperfections such as wrinkles, age spots or general unevenness of skin tone. Another preferred skin attribute is that of reduced shine. A shiny skin is indicative of oiliness which is an attribute disliked by many consumers. Most people prefer a matte appearance of their skin.

There has been considerable effort by the cosmetics industry to provide compositions which can mask or at least reduce skin imperfections. Often this is achieved by using materials such as talc, silica, kaolin and other inorganic particulates. These inorganic particulates achieve a matte effect due to their optical properties.

An alternative approach is referred to as achieving blurring effect. Here, the incoming light is distorted by scattering (lensing). Components of the cosmetic composition in this mechanism operate as lenses to bend and twist light in a variety of directions.

Unfortunately after the product with a blurring active is applied on skin, the blurring effect declines with the formation of sweat and oil on the skin over time. The present inventors have recognised that there remains a need to provide a composition which is capable of giving long lasting blurring effect to skin. Therefore, after extensive experimentation, they developed a personal care composition comprising specific porous particles in combination with specific film forming polymers in a cosmetically acceptable carrier, which has a longer lasting blurring efficacy.

SUMMARY OF THE INVENTION

In a first aspect, the present invention provides a personal care composition comprising
a) a porous particle;
b) a film forming polymer; and
c) a cosmetically acceptable carrier which is a water and oil emulsion;
wherein the porous particle has oil absorption value in the range of 50 g/100 g to 1500/100 g;
wherein the porous particle is selected from porous silica, cellulose, acrylic polymer, nylon and ethylene/methacylate copolymer hollow sphere coated with porous silica;
wherein the film forming polymer is selected from an acrylate polymer, a methacrylate polymer, a urethane polymer or co-polymers thereof; and
wherein the composition comprises whitening pigment in an amount of from 0.001 to 2 wt %.

In a second aspect, the present invention provides a method of improving the appearance of skin by providing improved blurring comprising the step of applying a composition of the present invention on the desired skin surface.

In a third aspect, the present invention provides use of composition of the present invention for reducing the appearance of fine lines, wrinkles, pores and/or blemish spots; evening skin tone, or a combination thereof on the desired skin surface.

All other aspects of the present invention will more readily become apparent upon considering the detailed description and examples which follow.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilized in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

By "A Personal Care Composition" as used herein, is meant to include a composition for topical application to the skin of mammals, especially humans. Such a composition may be generally classified as leave-on or rinse off but is preferably of the leave on type. The composition is formulated into a product which is applied to a human body specifically for improving appearance but may also be capable of providing cleansing, odor control or general aesthetics. The composition of the present invention can be in the form of a liquid, lotion, cream, foam, scrub, gel, or toner, or applied with an implement or via a face mask or a pad. Non-limiting examples of such compositions include leave-on skin lotions, creams, antiperspirants, deodorants, lipsticks, foundations, mascara, sunless tanners and sunscreen lotions. The composition of the present invention is preferably a leave-on composition. "Skin" as used herein is meant to include skin on the face and body (e.g., neck, chest, back, arms, underarms, hands, legs, buttocks and scalp) and especially to the sun exposed parts thereof.

"Film-forming polymer" as used herein refers to polymer which is capable of forming cohesive and continuous covering over the hair and/or skin when applied to their surface. Contact angle, as used herein, means the angle at which a water/vapor interface meets a solid surface at a temperature of 25° C. Such an angle may be measured with a goniometer or other water droplet shape analysis systems with water droplet of 5 μl and at 25° C. The requirement for film-forming polymer, as per the present invention is that the film-forming polymer is suitable to be employed in a cosmetic composition. The film-forming polymer, for use in the present invention, preferably has a contact angle of at least 85°, more preferably from 95° to 160°, most preferably from 100° to 120°. Not wishing to be bound by theory, the inventors believe that such a compact and continuous film covers the skin surface and helps to reduce the loss of the particles through abrasion. The film forming polymer is generally water insoluble and is distinct from water soluble polymers like cross-linked polyacrylic acid sold as Carbopol which are commonly used in cosmetic product as thickeners. The skilled person knows what is meant by the water-insolubility of a polymer. Preferably, the solubility of the polymer in water at 25° C. is less than 1 wt %, more preferably less than 0.5 wt %, even more preferably less than 0.1 wt % and most preferably less than 0.01 wt %.

The film forming polymer as per the invention is selected from an acrylate polymer, a methacrylate polymer, a urethane polymer or co-polymers thereof. Preferably, the film forming polymer as per the invention is selected from trimethylsiloxysilicate, polypropylsilsesquioxane, dimethicone/vinyltrimethylsiloxysilicate crosspolymer, acrylates/polytrimethylsiloxy methacrylate copolymer, C30 to 45 alkyldimethylsilyl polypropylsilsesquioxane and polyurethane. Commercially available film forming polymers which may be used in the present invention are Koboguard® 50N available from Kobo and BELSIL® REG 102 available from Wacker. Preferably, the film forming polymer is included in 0.1 to 10%, more preferably in 0.1 to 6%, most preferably in 1 to 3% by weight of the composition.

"Porous particle" as used herein refers to a particle with distributed voids throughout the entire volume of the particle. The voids can be individual or connected by small size openings, similar to pore openings that separate larger spaces.

"Average particle size" as used herein refers to the particle size in non-aggregated state unless otherwise stated. The average particle size, as per the present invention is apparent volume median diameter (d50, also known as x50 or sometimes d(0.5) of the particles measurable for example, by laser diffraction using a system such as a Mastersizer™ 2000 (available from Malvern Instruments Ltd) meeting the requirements set out in ISO 13320 unless otherwise stated. The d10 value denotes that 10% of the particles in the sample are below that particle size. d90 value denotes that 90% of the particles in the sample are below that particle size.

The requirement for porous particle of the present invention is that the porous particle has the capability of absorbing large amounts of oils. Preferably, the porous particle has an oil absorption value of higher than 50 g/100 g, more preferably higher than 200 g/100 g, and even more preferably higher than 300 g/100 g. The oil absorption value is preferably in the range of 50 g/100 g to 1500 g/100 g, more preferably in the range of 200 g/100 g to 1200 g/100 g and even more preferably in the range of 300 g/100 g to 1100 g/100 g. The oil absorption value refers to the values measured in conformity with ASTM Method D281-84.

The porous particle as per the invention has high pore volume to ensure the capability of oil absorption. Preferably, the pore volume value of the porous particle is higher than 0.02 $cm^3/g$ (0.02 cc/g), preferably higher than 0.7 $cm^3/g$ (0.7 cc/g), more preferably higher than 1.5 $cm^3/g$ (1.5 cc/g). The pore volume value is preferably in the range of 0.02 $cm^3/g$ (0.02 cc/g) to 7 $cm^3/g$ (7 cc/g), more preferably in the range of 0.7 $cm^3/g$ (0.7 cc/g) to 6 $cm^3/g$ (6 cc/g) and even more preferably in the range of 1.5 $cm^3/g$ (1.5 cc/g) to 5.6 $cm^3/g$ (5.6 cc/g). The pore volume value refers to the values measured in conformity with ASTM D4222-03.

The porous particle preferably has an average diameter of 200 nm to 50 microns, more preferably from 500 nm to 10 microns, and most preferably from 1 to 6 microns. To have a better sensory, the porous particle is preferably substantially uniform in size which means less than 5% of the porous particle have a diameter less than 0.5 times the average diameter and less than 5% of the porous particle have a diameter greater than 1.5 times the average diameter. In another aspect, the range of the diameter of the porous particle is preferably 0.8 to 1.2 times the average diameter, more preferably 0.9 to 1.1 times the average diameter.

The porous particle as per the invention is selected from porous silica, cellulose, acrylic polymer, nylon and ethylene/methacylate copolymer hollow sphere coated with porous silica or a mixture thereof.

Commercially available porous silica which may be used in the present invention are MSS-500/3H® and MSS-500/H® from Kobo. Commercially available porous nylon which may be used in the present invention are TR-1®, TR-2®, SP-10® and SP-500® from Kobo. Commercially available porous cellulose which may be used in the present invention is CELLULOBEADS® USF from Daito Kasei. Commercially available ethylene/methacylate copolymer hollow sphere coated with porous silica which may be used in the present invention are DSPCS/3H-12® and DSPCS/H-12® from Kobo.

Preferably, the porous particle is present in the composition in amount of from 0.1 to 10% by weight of the composition, more preferably from 1 to 3% by weight of the composition.

The composition may optionally additionally comprise a silicone elastomer. The silicone elastomer used in the present invention is preferably powder of silicone elastomer. It is highly preferred that the silicone elastomer is cross-linked. Preferred silicone elastomers are organo-polysiloxanes available under the INCI names of dimethicone/vinyl dimethicone crosspolymer, dimethicone crosspolymer and Polysilicone-11®. More preferably the silicone elastomer is dimethicone/vinyl dimethicone crosspolymer.

Typically, the average diameter of the silicone elastomer is from 0.2 to 50 microns, more preferably from 0.5 to 20 microns, even more preferably from 0.8 to 10 microns, and still even more preferably from 1.5 to 6 microns.

The silicone elastomer is preferably present in amount of 0.5 to 20%, more preferably 1 to 15%, even more preferably from 2 to 6%, still even more preferably from 4.5 to 9% by weight of the composition.

The composition additionally comprises a whitening pigment. The whitening pigment are typically particles of high refractive index materials. For example the whitening pigment may have a refractive index of greater than 1.3, more preferably greater than 1.8 and most preferably from 2.0 to 2.7. Examples of such whitening pigment are those comprising bismuth oxy-chloride barium sulfate, mica, silica, titanium dioxide, zirconium oxide, aluminum oxide, zinc oxide or combinations thereof. More preferred whitening pigment are particles comprising titanium dioxide, zinc oxide, zirconium oxide, mica, iron oxide or a combination thereof. Even more preferred whitening pigment are particles comprising zinc oxide, zirconium oxide, titanium dioxide or a combination thereof as these materials have especially high refractive index. Still even more preferably the whitening pigment is selected from titanium dioxide, zinc oxide or a mixture thereof and most preferred whitening pigment is titanium dioxide.

The average diameter of whitening pigment is typical from 15 nm to 2 microns, more preferably from 35 nm to 800 nm, even more preferably from 50 nm to 500 nm and still even more preferably from 100 to 300 nm. Diameter of whitening pigment refers to the diameter of particles in an un-aggregated state. In the event a well-defined sphere is not generated, diameter means the largest measurable distance on a particle The average diameter may be measured for example by scanning electron microscopy (SEM) or transmission electron microscopy (TEM) by averaging the value of at least one hundred particles.

The composition as per the invention comprises whitening pigment in an amount of from 0.001 to 2 wt %.

The composition preferably additionally comprises one or more organic sunscreens. A wide variety of organic sunscreen is suitable for use in combination with the essential ingredients of this invention. Suitable UV-A/UV-B sunscreen include, 2-hydroxy-4-methoxybenzophenone, octyldimethyl p-aminobenzoic acid, digalloyltrioleate, 2,2-dihydroxy-4-methoxybenzophenone, ethyl-4-(bis(hydroxypropyl)) aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, 2-ethylhexyl-p-methoxycinnamate, butylmethoxydibenzoylmethane, 2-hydroxy-4-methoxybenzophenone, octyldimethyl-p-aminobenzoic acid and mixtures thereof. The most suitable organic sunscreens are 2-ethylhexyl-p-methoxycinnamate, butylmethoxydibenzoylmethane or a mixture thereof.

A safe and effective amount of organic sunscreen may be used in the compositions useful in the subject invention. The composition preferably comprises from 0.1% to 10%, more preferably from 0.1% to 5%, of organic sunscreen.

The composition of the invention preferably comprises a skin lightening agent. Vitamin B3 compounds (including derivatives of vitamin B3) e.g. niacin, nicotinic acid or niacinamide are the preferred skin lightening agent as per the invention, most preferred being niacinamide. Vitamin B3 compounds, when used, are preferably present in an amount in the range of 0.1 to 10%, more preferably 0.2 to 5% by weight of the composition.

The composition may comprise other beneficial skin care actives like retinol, retinyl esters, resorcinol, allantoin, ubiquinone, conjugated linoleic acid, 12-hydroxystearic acid or derivatives thereof. Of these the most preferred ones for inclusion in the composition of the invention are anti-aging actives like retinol or retinyl esters.

Compositions of the present invention will also include a cosmetically acceptable carrier which is a water and oil emulsion, which in certain embodiments may be water-in-oil emulsion. Preferred emulsions, however, are the oil-in-water variety.

Preferred hydrophobic material for use in the oil phase of such emulsions includes emollients such as fats, oils, fatty alcohols, fatty acids, soaps, silicone oils, synthetic esters and/or hydrocarbons.

Silicones may be divided into the volatile and nonvolatile variety. Volatile silicone oils (if used) are preferably chosen from cyclic (cyclomethicone) or linear polydimethylsiloxanes containing from 3 to 9, preferably from 4 to 5, silicon atoms.

Nonvolatile silicones useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to 0.1 m$^2$/s at 25° C. Among the preferred nonvolatile emollients useful in the present compositions are the polydimethyl siloxanes having viscosities from about $1 \times 10^{-5}$ to about $4 \times 10^{-4}$ m$^2$/s at 25° C.

Specific examples of non-silicone emollients include stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rape seed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate, and mixtures thereof.

Among the ester emollients are:
a) Alkenyl or alkyl esters of fatty acids having 10 to 20 carbon atoms. Examples thereof include isoarachidyl neopentanoate, isodecyl neopentanoate, isononyl isonanoate, cetyl ricinoleate, oleyl myristate, oleyl stearate, and oleyl oleate;
b) Ether-esters such as fatty acid esters of ethoxylated fatty alcohols;
c) Polyhydric alcohol esters. Butylene glycol, ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of 01-030 alcohols. An Example is pentaerythrityl tetraethylhexanoate;

d) Wax esters such as beeswax, spermaceti wax and tribehenin wax;

e) Sterols esters, of which cholesterol fatty acid esters are examples thereof;

f) Sugar ester of fatty acids such as sucrose polybehenate and sucrose polycottonseedate; or g) mixtures of two or more of the foregoing (a) to (f).

Of particular use also are the 012-15 alkyl benzoate esters sold under the Finsolv® brand.

Hydrocarbons which are suitable emollients include petrolatum, mineral oil, $C_{11}$-$C_{13}$ isoparaffins, polyalphaolefins, isohexadecane or a mixture thereof.

Amounts of water in the carrier may, for example, range from 1 to 99%, more preferably from 5 to 90%, even more preferably from 35 to 80%, optimally between 40 and 70% by weight of the personal care composition.

Other materials which can be included in the cosmetically acceptable carrier include solvents, humectants, thickeners and powders. Examples of each of these types of material, which can be used singly or as mixtures, are as follows: Solvents include ethyl alcohol, isopropanol, acetone, ethylene glycol monoethyl ether, diethylene glycol monobutyl ether, diethylene glycol monoethyl ether and mixtures thereof.

Humectants include those of the polyhydric alcohol-type. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, glycerol, ethoxylated glycerol, propoxylated glycerol and mixtures thereof. The amount of humectant may range, for example, anywhere from 0.5 to 50%, more preferably between 1 and 15% by weight of the composition. Most preferred is glycerol (also known as glycerin). Amounts of glycerin may range, for example, from 0.5% to 50%, more preferably from 1 to 35%, optimally from 2 to 15% by weight of the composition.

A variety of thickening agents may be included in the compositions. Illustrative but not limiting are stearic acid, Acrylamide/Sodium Acryloyldimethyltaurate Copolymer (Aristoflex® AVC), Hydroxyethyl Acrylate/Sodium Acryloyldimethyltaurate Copolymer, Aluminum Starch Octenyl Succinate, Polyacrylates (such as Carbomers including Carbopol® 980, Carbopol® 1342, Pemulen TR-2® and the Ultrez® thickeners), Polysaccharides (including xanthan gum, guar gum, pectin, carageenan and sclerotium gums), celluloses (including carboxymethyl cellulose, ethyl cellulose, hydroxyethyl cellulose and methyl hydroxymethyl cellulose), minerals (including talc, silica, alumina, mica and clays, the latter being represented by bentonites, hectorites and attapulgites), magnesium aluminum silicate and mixtures thereof. Amounts of the thickeners may range, for example, from 0.05 to 10%, more preferably from 0.3 to 2% by weight of the composition.

Powders include chalk, talc, Fullers earth, kaolin, starch, gums, colloidal silica sodium polyacrylate, tetraalkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose and ethylene glycol monostearate.

The personal care composition of this invention is preferably a skin care composition. More preferably, the composition is preferably an antiperspirant composition or a face (except eye lids and lips) care composition. The skin care composition refers to a composition suitable for topical application to human skin, including leave-on and wash-off products. Preferably the term encompasses a fluid or liquid, and particularly a moisturizer rather than a make-up product. Most preferred are leave-on compositions. The term "leave-on" as used with reference to compositions herein means a composition that is applied to or rubbed on the skin, and left thereon. The term "wash-off" as used with reference to compositions herein means a skin cleanser that is applied to or rubbed on the skin and rinsed off substantially immediately subsequent to application. The term "skin" as used herein includes the skin on the face (except eye lids and lips), neck, chest, abdomen, back, arms, under arms, hands, and legs. Preferably the term "skin" includes the skin on the face (except eye lids and lips) and under arms. More preferably it means skin on the face other than lips and eyelids.

The composition can be formulated in any known format, more preferred formats being creams or lotions.

Packaging for the composition of this invention can be a jar or tube as well as any other formats typically seen for cosmetic, cream, washing and lotion type products. The compositions may be applied topically and preferably 1-4 milligrams of composition is applied per square centimeter of skin.

The composition of the invention preferably delivers a cosmetic benefit to the skin of an individual to which it is topically applied. Examples of cosmetic benefits include reducing the appearance of fine lines, wrinkles, pores and/or blemish spots; evening skin tone, long lasting optical effect or a combination thereof on the desired skin surface.

The following examples are provided to facilitate an understanding of the invention. The examples are not intended to limit the scope of the claims.

EXAMPLES

| | | Materials | | | |
|---|---|---|---|---|---|
| Trade name | INCI name | Supplier | Diameter (microns) | Oil Absorption (Linseed oil g/100 g) | Pore volume (cc/g) |
| MSS-500/3H | Silica (Porous) | KOBO | 3 | 305 | 1.547 |
| MSS-300/3N | Silica (Solid) | KOBO | 5.5 | 31.8 | 0.0163 |
| Makibeads 80 | Methyl Methacrylate Crosspolymer | Daito Kasei | 7 | 110 | 0.3951 |

-continued

| | | Materials | | | |
|---|---|---|---|---|---|
| Trade name | INCI name | Supplier | Diameter (microns) | Oil Absorption (Linseed oil g/100 g) | Pore volume (cc/g) |
| DC9509 (63% solid active) | Dimethicone/Vinyl-dimethicone Crosspolymer (and) C12-14 Pareth-12 | Dow Corning | 3 | | |
| BELSIL ® REG 102 | Cyclopentasiloxane, dimethicone/vinyl-trimethylsiloxy-silicate crosspolymer | Wacker | — | — | |
| Koboguard ® 50N | Acrylates/ethyl-hexyl acrylate copolymer | KOBO | — | | |

Example 1: Effect of the Combination of Porous Particle and Film Forming Polymer on the Blurring Efficacy A series of skin care compositions were formulated as shown in Table 1.

TABLE 1

| Ingredient (active wt %) | Samples | | | |
|---|---|---|---|---|
| | A | B | 1 | C |
| Water | Bal. | Bal. | Bal. | Bal. |
| MSS-500/3H | 0 | 0 | 3.00 | 0 |
| MSS-300/3N | 0 | 0 | 0 | 3.00 |
| DC9509 | 8.00 | 8.00 | 8.00 | 8.00 |
| BELSIL ® REG 102 | 0 | 2.00 | 2.00 | 2.00 |
| Tween 20 | 1.00 | 1.00 | 1.00 | 1.00 |
| Glycerin | 2.00 | 2.00 | 2.00 | 2.00 |
| Cyclopentasiloxane (D5) | 12.00 | 12.00 | 12.00 | 12.00 |
| Simulgel ® EG | 2.00 | 2.00 | 2.00 | 2.00 |
| Preservative | 0.476 | 0.476 | 0.476 | 0.476 |

The performance of the personal care compositions in Table 1 above was measured using an in vitro model as given below.

(1) Measurement of Gloss of the Artificial Skin Before and after Application

Wrinkled Bio-skin plates (BP-EW1 #BSC, Beaulax Co., Ltd., Tokyo, Japan) made of polyurethane elastomer were used as substrate to mimic the human skin with wrinkles. A dual-polarized image system called SAMBA (Bossa Nova Technologies, USA) was employed to measure the gloss degree of the wrinkled Bio-skin plates by following the method and principle described by Akira Matsubara [Skin translucency: what is it and how is it measured, The International Federation of Societies of Cosmetic Chemists (IFSCC) Congress 2006, Osaka, Japan]. A software named SAMBA face system (Version 4.3) was equipped for the analysis. The Wrinkled Bio-skin plates were tested against an incident light with exposure time of 80 msec. The operation mode was parallel polarization and crossed polarization modes.

Then, 28 mg of one sample as prepared in Example 1 was applied to and spread by finger cot within the circle with area of 7 cm² for gloss test and wait for 30 minutes to dry naturally. The gloss of the wrinkled Bio skin plates after the samples were applied were measured again using the SAMBA system.

(2) Calculation of L&W index

The incident light was reflected and scattered by Bio-skin plates. The specular reflected light kept the same polarization as the incident light whereas the scattering light from the volume (diffused light) was un-polarized. The SAMBA® camera acquired successively two images corresponding to two states of polarization (parallel and crossed). The parallel image intensity (P) is contributed from both the reflected and scattered light, and the crossed image intensity (C) is contributed from the scattered light only. The parallel image plus the crossed image is equal to the total image delivered by a traditional camera or perceived by human eye.

The gloss degree was calculated by (P−C)/(P+C). The calculation of gloss degree was performed for each pixel. The standard deviation (STD) of gloss degree is a measure of the uniformity of the skin appearance. The higher the STD is, the lower the uniformity is. Herein we defined a L&W (line and wrinkle) index to demonstrate degree of blurring efficacy of the skin care composition. The L&W index was calculated by (STD of gloss degree before applying sample—STD of gloss degree after applying sample)/(STD of gloss degree before applying sample). The higher the L&W index is, the higher is the blurring efficacy of the sample.

(3) Protocol of Oil/Water Co-Deposition Mimicking Sebum/Sweat Secretion

The secretion of sebum or sweat was simulated by the humidifiers, to generate fine oil or water droplets, which will deposit on the top of BSP. Two humidifiers were employed, one for spraying oil mist and the other for water mist. The wrinkle BSP was left in the chamber where the humidifiers were placed for the accumulation of oil/water. The L&W index was measured after each deposition.

The data of blurring efficacy is listed in Table 2 below.

TABLE 2

| Sample | Instant L&W index | L&W index after oil/water deposition |
|---|---|---|
| A | 20.37% ± 5.3% | −34.81% ± 6.50% |
| B | 23.50% ± 2.2% | 17.04% ± 1.58% |
| 1 | 40.32% ± 3.2% | 41% ± 0.7% |
| C | 21.48% ± 1.1% | 0% ± 5.7% |

Table 2 shows the test results of the instant L&W index and L&W index after oil/water deposition. The data indicates that the composition 1 has both higher instant and long-lasting efficacy than composition containing only silicone particle (Sample 1 vs. Sample A), composition containing silicone particle with film forming polymer (Sample 1 vs. Sample B) and composition containing solid particle replacing porous particle (Sample 1 vs. C). It is surprisingly found that porous particle with film forming polymer is capable of synergistically boosting the blurring efficacy.

Example 2: Antirub-Off Efficacy of Combination of Porous Particle and Film Forming Polymer A series of skin care compositions were formulated as shown in Table 3.

TABLE 3

| Ingredient (active wt %) | Samples | | |
|---|---|---|---|
| | D | 2 | 3 |
| Water | Bal. | Bal. | Bal. |
| Makibeads 80 | 3 | 3 | 3 |
| DC9509 | 8.00 | 8.00 | 8.00 |
| BELSIL ® REG 102 | 0 | 2.00 | 0 |
| Koboguard ® 50N | 0 | 0 | 2.00 |
| Tween 20 | 1.00 | 1.00 | 1.00 |
| Glycerin | 2.00 | 2.00 | 2.00 |
| Cyclopentasiloxane (D5) | 12.00 | 12.00 | 12.00 |
| Simulgel EG | 2.00 | 2.00 | 2.00 |
| Preservative | 0.476 | 0.476 | 0.476 |

The performance of the personal care compositions in Table 3 above was measured using an in vitro model as given below.

The brushing instrument (M235 Martindale®, SDLATLAS) was employed to mimic rubbing effect. The test procedure was described as below:

Step 1: The product was applied on a wrinkle BSP at a dose of 4 mg/cm$^2$, and allowed to dry for 15 min;

Step 2: The initial L&W index was measured using method described in Example 1.

Step 3: Then the wrinkle BSP was put on the plate and rubbed with a probe for 30 counters at speed 59.4 rpm using brushing instrument (WIRA, SDLATLAS).

Step 4: The L&W index was measured after being rubbed.

The difference between these 2 L&W index is calculated, coded as Delta L&W index. Delta L&W index after rubbing=L&W index (after)−L&W index (baseline). The smaller value, the higher resistance to rubbing effect.

The data of blurring efficacy is listed in Table 4 below.

TABLE 4

| Sample | Delta L&W index after rubbing |
|---|---|
| D | −6.56% ± 2.13% |
| 2 | −1.81% ± 0.85% |
| 3 | −1.44% ± 1.21% |

Table 4 shows the test results of the antirub-off efficacy. The data indicates that the composition 2 and composition 3 has better resistance to rub-off than composition containing silicone particle with porous particle (Sample 2 vs. Sample D, Sample 3 vs. Sample D). It is surprisingly found that porous particle with film forming polymer is capable of synergistically boosting the long lasting blurring efficacy.

Example 3: Blurring Efficacy of the Combination of Porous Particle and Film Forming Polymer v/s Commercial Products Two skin care commercial samples were included in the test as shown in Table 5.

TABLE 5

| | Commercial Sample |
|---|---|
| E | L'Oreal Revitalift ® Daily Anti-wrinkle moisturizer (emulsion) |
| F | L'Oreal Revitalift ® Magic Blur Instant smoother (anhydrous) |

The instant L&W index and L&W after oil/water deposition of samples were tested using method described in Example 1.

The sensory of samples was measured using an in vitro model as given below. Rheology measurement method:

Strain Sweep Mode

The strain sweep measurements were performed by a stress-controlled rheometer (Physica® MCR501 from Anton Paar, Austria) equipped with the customized software RHEOPLUS/32 V2.81 under oscillation mode. The sample was loaded between parallel plates (PP25S) with sandy surface to reduce the slippery phenomenon during the measurement. The gap size was set to be 0.5 mm. Excess samples at the plate edge were trimmed. The measurements were conducted logarithmically with strain from 0.01% to 1000% and fixed frequency of 10 rad/s. The temperature was set to be 25° C. After loading, the sample was allowed to settle for 3 min for stress relaxation. The data was collected in logarithmic steps with 10 points per decade.

Storage modulus G' was used to characterize the viscoelastic properties of the samples. Specifically, G' is related with product hardness. Here G' stands for G'_plateau for short. It was obtained by the strain sweep measurement through software RHEOPLUS/32 V2.81. G' is the average of G' values that were recorded in the viscoelastic regime. In this case, the regime varied from strain 0.01% to 1%.

Steady Shear Mode

A stress-controlled MCR 501 (from Anton Par, Physica MCR501, Austria) rheometer fitted with a sandblast parallel geometry (PP25s) was used to monitor the rheological data between shear rate range 0.01 1/s to 1000 1/s. The gap between the upper plate and the lower plate was kept as 0.5 mm. The temperature was set with 25° C. Excess samples at the edge of the plate were trimmed. After loading, the sample was allowed to settle for 3 min for stress relaxation. The data was collected in logarithmic steps with 10 points per decade.

The yield stress was obtained by the steady shear measurement. The actual value was calculated by fitting Herschel-Bulkley model to the shear stress and shear rate data.

The data of blurring efficacy and rheology is listed in Table 6 below.

TABLE 6

| Sample | Instant L&W index | L&W index after oil & water deposition | G' (Pa) | Yield stress (Pa) |
|---|---|---|---|---|
| 1 | 40.32% ± 3.2% | 41% ± 0.7% | 2146.5 | 257.7 |
| E | 13.78% ± 0.9% | 15% ± 4.2% | 1882.9 | 468.7 |
| F | −50.39% ± 8.5% | 9.75% ± 21.6% | 1910.8 | 325.6 |

Table 6 shows the test results of the blurring efficacy and sensory benefit. The data indicates that the composition 1 has both higher instant and long lasting efficacy than the commercial products (Sample 1 vs. Sample E, Sample 1 vs. Sample F). It is also found that the composition 1 has higher storage modulus (G') and lower yield stress, indicating better sensory in-use.

Example 4: Impact of Dosage of Whitening Pigments in the Composition as Per the Invention on the Blurring Efficacy A series of skin care compositions were formulated as shown in Table 7.

TABLE 7

| | Samples | | |
|---|---|---|---|
| Ingredient (active wt %) | 4 | 5 | G |
| Water | Bal. | Bal. | Bal. |
| MSS-500/3H | 3.00 | 3.00 | 3.00 |
| Mica (MearlMica II from BASF) | 0.20 | 2.00 | 12.00 |
| DC9509 | 8.00 | 8.00 | 8.00 |
| BELSIL ® REG 102 | 2.00 | 2.00 | 2.00 |
| Tween 20 | 1.00 | 1.00 | 1.00 |
| Glycerin | 2.00 | 2.00 | 2.00 |
| Cyclopentasiloxane (D5) | 12.00 | 12.00 | 12.00 |
| Simulgel EG | 2.00 | 2.00 | 2.00 |
| Preservative | 0.476 | 0.476 | 0.476 |

The instant L&W index of each sample was tested using the method described in Example 1. The data of blurring efficacy is listed in Table 8 below.

TABLE 8

| Sample | Instant L&W index |
|---|---|
| 4 | 39.36% ± 1.2% |
| 5 | 29.1% ± 1.6% |
| G | −15.85% ± 0.6% |

The data indicates that the compositions as per the invention (Samples 4 and 5) have higher instant blurring efficacy when low amounts of whitening pigment (Mica) are included, as compared to when high amount of whitening pigment is included (Sample G).

The invention claimed is:

1. A personal care composition comprising:
   a) a porous particle;
   b) a dimethicone/vinyltrimethylsiloxysilicate film forming crosspolymer;
   c) a cosmetically acceptable carrier which is a water and oil emulsion;
   d) 4.5 to 9% of a silicone elastomer by weight of the personal care composition;
   e) 0.001 to 2% of a whitening pigment by weight of the personal care composition selected from the group consisting of titanium dioxide, zinc oxide, zirconium oxide, and a mixture thereof, wherein the porous particle has oil absorption value in the range of 50 g/100 g to 1500 g/100 g and pore volume higher than 0.02 cm$^3$/g;

and further wherein the film forming crosspolymer has a contact angle of at least 85°; and the porous particle is selected from the group consisting of porous silica, cellulose, acrylic polymer, nylon and a porous silica-coated ethylene/methacrylate copolymer hollow sphere.

2. The personal care composition as claimed in claim 1, wherein the oil absorption value of the porous particle is 300 g/100 g to 1100/100 g.

3. The personal care composition as claimed in claim 1, wherein the porous particle is selected from porous silica and acrylic polymer.

4. The personal care composition as claimed in claim 1, wherein the pore volume of the porous particle is higher than 0.02 cm$^3$/g (0.02 cc/g).

5. The personal care composition as claimed in claim 1, wherein the porous particle has an average size from 200 nm to 50 microns.

6. The personal care composition as claimed in claim 1, wherein the porous particle is present in amount of 0.1 to 10%, by weight of the personal care composition.

7. The personal care composition as claimed in claim 1, wherein the dimethicone/vinyltrimethylsiloxysilicate film forming crosspolymer is present in amount of 0.1 to 10% by weight of the personal care composition.

8. The personal care composition as claimed in claim 1, wherein the whitening pigment has a refractive index of greater than 1.3.

9. The personal care composition as claimed in claim 1, wherein the silicone elastomer is a dimethicone/vinyl dimethicone crosspolymer.

10. The personal care composition as claimed in claim 1, wherein the cosmetically acceptable carrier is an oil-in-water emulsion.

11. The personal care composition as claimed in claim 1, wherein the pore volume of the porous particle is higher than 0.7 cm$^3$/g (0.7 cc/g).

12. The personal care composition as claimed in claim 1, wherein the pore volume of the porous particle is higher than 1.5 cm$^3$/g (1.5 cc/g).

13. The personal care composition as claimed in claim 1, wherein the porous particle has an average size from 500 nm to 10 microns.

14. The personal care composition as claimed in claim 1, wherein the porous particle has an average size from 1 micron to 6 microns.

15. The personal care composition as claimed in claim 1, wherein the porous particle is present in amount of 0.5 to 3.5% by weight of the personal care composition.

16. The personal care composition as claimed in claim 1, wherein the dimethicone/vinyltrimethylsiloxysilicate film forming crosspolymer is present in amount of 1 to 3% by weight of the personal care composition.

17. The personal care composition as claimed in claim 1, wherein the whitening pigment is titanium dioxide, zinc oxide, or a mixture thereof.

* * * * *